United States Patent [19]

Shikinai et al.

[11] 4,003,423
[45] Jan. 18, 1977

[54] METHODS AND MEANS FOR MAKING DENTAL CASTINGS AND THE LIKE

[75] Inventors: Tadaomi J. Shikinai, Tokyo, Japan; Robert A. Horton, Chesterland, Ohio

[73] Assignee: Precision Metalsmiths, Inc., Cleveland, Ohio

[22] Filed: June 9, 1975

[21] Appl. No.: 585,068

[52] U.S. Cl. .................................. 164/34; 164/241; 164/244; 164/246; 164/DIG. 4
[51] Int. Cl.² ....................... B22C 9/02; B22C 7/04; B22C 7/00
[58] Field of Search ............... 164/34, DIG. 4, 235, 164/241, 242, 244, 246, 247

[56] References Cited

UNITED STATES PATENTS

| | | | |
|---|---|---|---|
| 3,424,227 | 1/1969 | Watts et al. | 164/34 |
| 3,648,760 | 3/1972 | Cooper | 164/DIG. 4 |
| 3,669,177 | 6/1972 | Ingalls et al. | 164/34 |
| 3,756,553 | 9/1973 | Ranz | 164/341 |
| 3,868,986 | 3/1975 | Olsen | 164/34 |

*Primary Examiner*—Harrison L. Hinson
*Attorney, Agent, or Firm*—Watts, Hoffmann, Fisher & Heinke Co.

[57] ABSTRACT

A pattern set-up especially useful for making prosthetic dental appliances is assembled by attaching a plurality of refractory casts to a support member so that adjacent casts along the length of the support member are circumferentially offset with respect to one another. The casts carry expendable patterns that are connected to the support member by gating systems laid down on faces of the casts. The support member has outward protrusions supporting the weight of the casts and may be formed by a plurality of segments fitted together in end-to-end relation.

14 Claims, 8 Drawing Figures

METHODS AND MEANS FOR MAKING DENTAL CASTINGS AND THE LIKE

BACKGROUND OF THE INVENTION

The present invention relates generally to the lost pattern process of investment casting, and more specifically to investment casting methods and pattern set-ups that are especially useful for making dental castings and the like.

The invention is particularly concerned with the manufacture of prosthetic dental appliances. A conventional practice of making dental appliances has generally involved the steps of producing a refractory cast of anatomical form duplicating the oral structure of the patient. A wax or plastic pattern of the prosthetic appliance is laid down on the cast and a sprue and gating system is attached to the pattern. The assembly is then covered or invested with refractory material to form a mold. After the mold has dried, the pattern is eliminated, as by heating and melting, and a suitable metal, such as gold or chrome alloy, is introduced into the resulting cavity to form the appliance casting. This general procedure is illustratively described with greater detail in U.S. Pat. Nos. 2,461,416 and 3,192,583.

In carrying out the conventional practice described above, it has been customary to invest a single refractory cast in a mold and to introduce the molten metal into the mold either statically or centrifugally. In the case of static casting operations, the sprue and gating system has been arranged to extend vertically with respect to the pattern and the refractory cast. One explanation for the usual procedure of investing a single cast in a mold is that the casts are relatively heavy and awkward to handle. Because of their shape and weight, it is difficult for an operator to attach several casts to a single support in the manner customarily done with investment casting patterns. Also, the refractory casts may fall off or be knocked from the conventional pattern support members during handling and investing.

SUMMARY OF THE INVENTION

The present invention is concerned with new and useful improvements in the art of investment casting which make it commercially practical to invest a plurality of refractory dental models in single mold. The invention is particularly concerned with a new support member which is specially constructed to support a plurality of dental models and to facilitate the operations of attaching the models and investing refractory material around them to make a mold.

In accordance with a preferred embodiment of the invention, a plurality of dental models are clustered about and attached to a center support member to form a set-up. Each model includes an anatomic refractory cast which carries an expendable pattern that is a replica of the prosthetic dental appliance to be cast in metal. A gating system connects the pattern to the support member.

Preferably, the refractory casts are arranged on the support member so that adjacent casts along the length of the support member are circumferentially offset with respect to one another. This arrangement provides the spacing between the casts which is necessary to the formation of a strong, satisfactory mold. The investment material of the mold can be packed between and around the casts to form a mold wall that will resist cracking when the mold is filled with metal. The offset spacing of the casts also facilitates the operation of mounting them on the support member.

The support member is constructed to include a plurality of outwardly extending protrusions which support the models so that they will not fall off the support member during handling. In a preferred embodiment, the support member construction further comprises a plurality of segments which are fitted together in end-to-end relation. The segmental construction facilitates assembly of the set-up. It is easier to connect the models to the individual segments before they are fitted together than it is to connect the models to a single, unitary support member.

A further advantage of constructing the support member in segments is that it provides a simple and convenient method of circumferentially offsetting the outwardly extending protrusions without requiring expensive tooling to form the support member. The individual segments do not have any undercuts which would require special provision in the tooling to release them as would be the case if the entire support member were a unitary structure. Further, the segments can be injection molded using smaller and less expensive machines than would be required to inject a unitary support member.

Other advantages and a fuller understanding of the invention will be had from the following detailed description when taken in conjunction with the accompanying drawings.

DESCRIPTION OF THE PREFERRED EMBODIMENT

Figure 1:
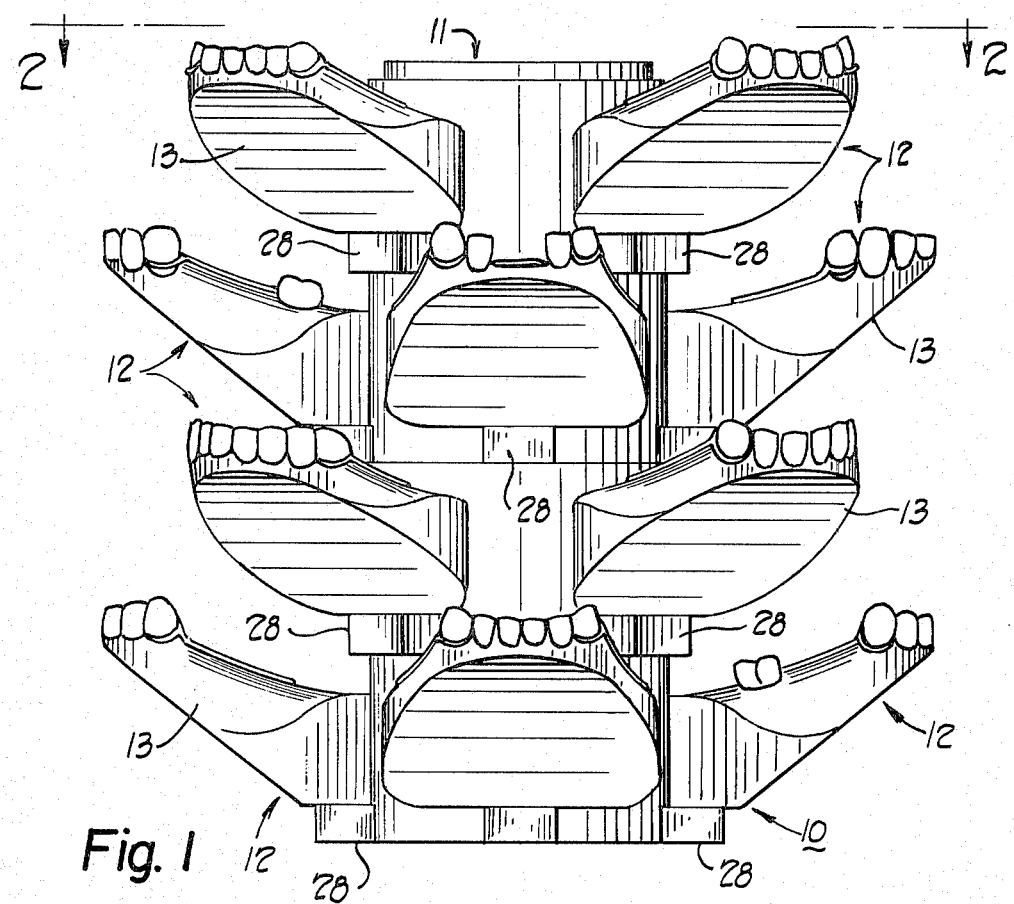
FIG. 1 is an elevational view of a set-up assembly according to the present invention.
Figure 2:
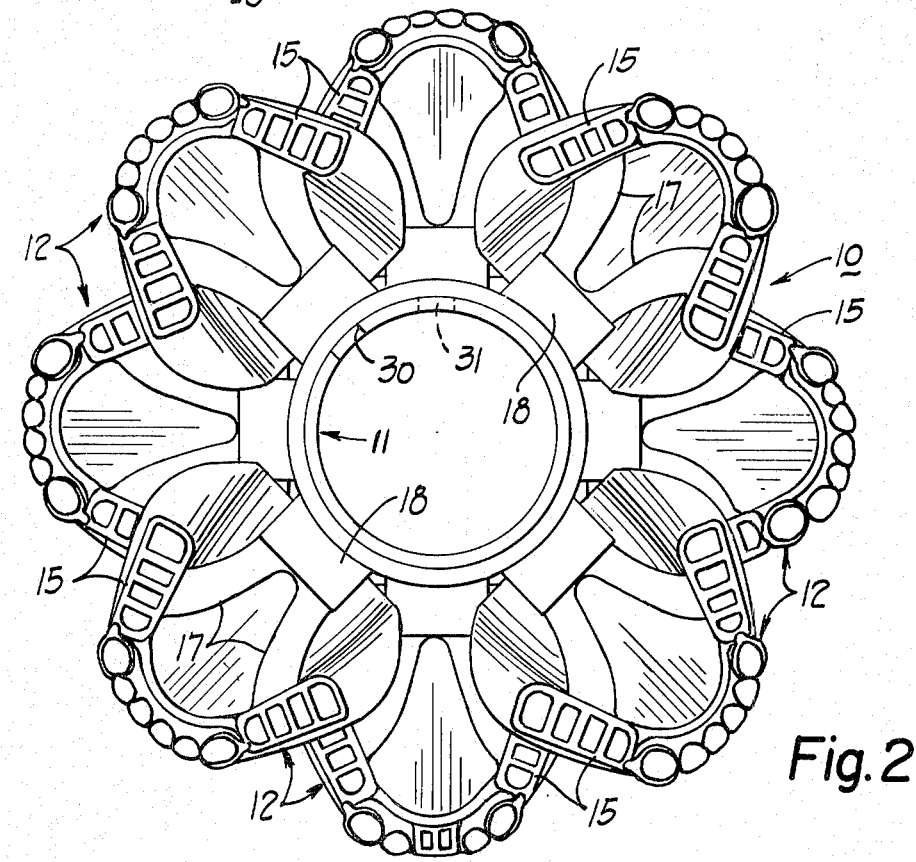
FIG. 2 is a top plan view of the assembly shown in FIG. 1.

Referring now to the drawings, and to FIGS. 1 and 2 in particular, a set-up assembly constructed in accordance with the present invention is generally designated by reference 10. The set-up 10 is generally comprised of a center support member 11 and a plurality of models 12 clustered around the outside of the support member. As shown, the support member 11 is in the form of a hollow cylinder. It is to be understood, however, that the support member 11 may be solid and that it may be of any desired cross-sectional shape, such as rectangular, triangular, square, hexagonal, etc.

Figure 3:
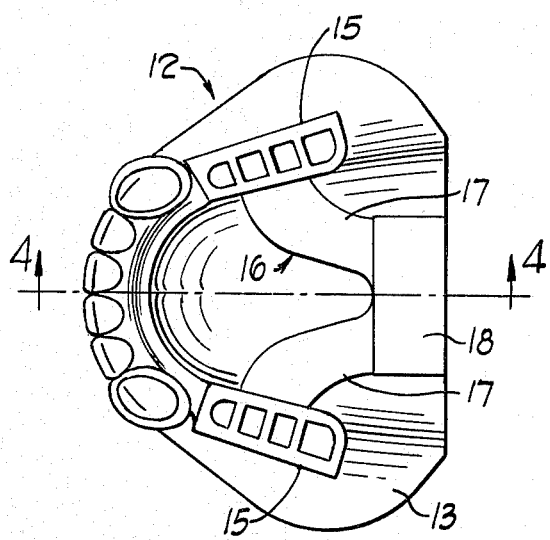
FIG. 3 is a top plan view of an exemplary dental model.
Figure 4:
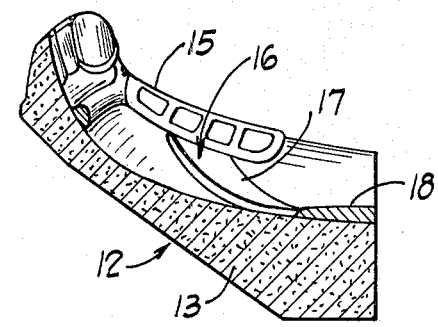
FIG. 4 is a cross-sectional view taken substantially on the line 4—4 of FIG. 3.

The models 12 comprise refractory casts 13 of oral structures. These casts are made in accordance with conventional practices and do not form a part of the present invention. A pattern 15 of any desired shape duplicating the particular dental appliance to be cast in metal is carried by each of the refractory casts 13, as is best shown in FIGS. 2 and 3. The patterns 15 may be formed of any suitable expendable material used in the investment casting industry, preferably a soft, pliable wax or the like.

A gating system 16 is connected to each of the patterns 15. Each gating system 16 is preferably formed by laying down strips of wax or the like along a face of the cast 13. As is shown most clearly in FIG. 3, the exemplary gating system 16 is generally Y-shaped and comprises a pair of arms 17 which terminate in a stem 18 located at one end of the cast 13.

The models 12, each including the cast 13, the pattern 15 and the gating system 16, are arranged about the support member 11 so that adjacent models along the length of the support member are circumferentially offset with respect to one another. It will be seen from FIG. 1 that this arrangement provides open areas above and below each model. These open areas assure that refractory investment material can be filled in around the models to form a strong, void-free mold.

Figure 6:
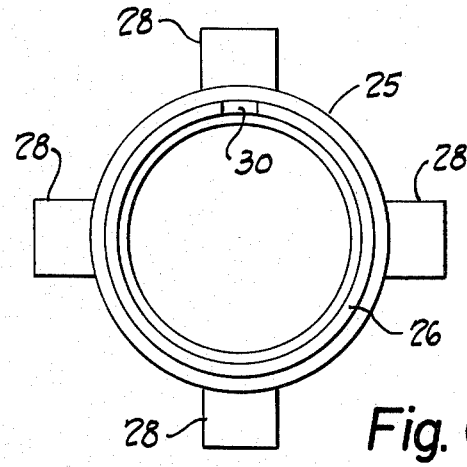
FIG. 6 is a top plan view of the support member taken along the line 6—6 of FIG. 5.
Figure 5:
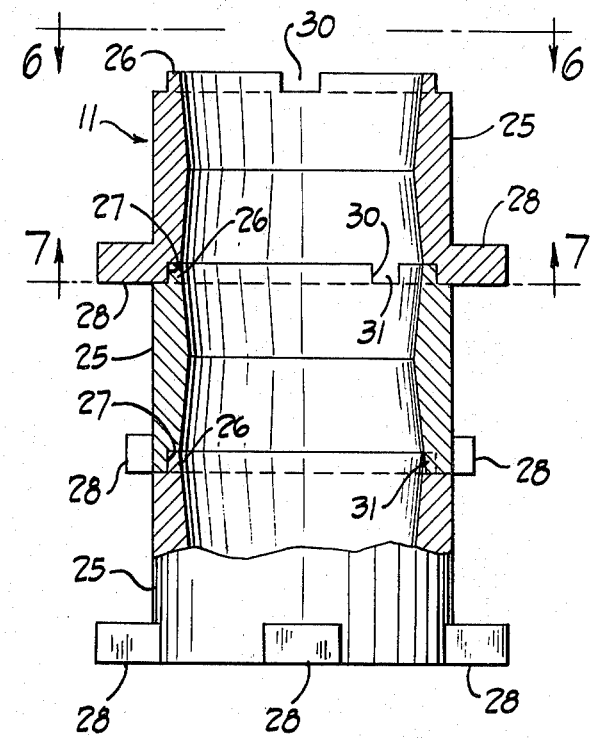
FIG. 5 is a vertical cross-sectional view of the center support member of the set-up.
Figure 7:
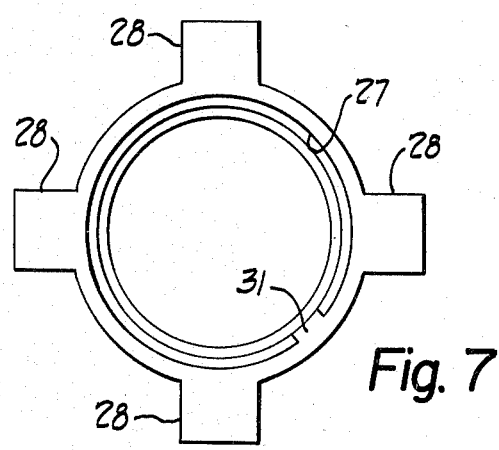
FIG. 7 is a horizontal cross-sectional view taken on the line 7—7 of FIG. 5.

Referring now to FIGS. 5–7, the illustrated support member 11 is comprised of a plurality of identical cylindrical segments 25 fitted together in end-to-end relation. The segments 25 may be injection molded from an expendable material, such as wax, a synthetic resin, or a wax and synthetic resin combination. As shown, the inner surfaces of the segments 25 taper axially radially inwardly from each end. The purpose of the double taper is to facilitate removal of the segments from the injection die. It is to be understood, however, that the taper could be eliminated if desired.

Each of the cylindrical segments 25 has a neck 26 at one end and is notched to form a circular recess 27 at the other end. The recesses 27 are shaped to receive the necks 26 so that the segments 25 can be fitted together to form a continuous tube. Each segment 25 further includes a plurality of circumferentially spaced protrusions 28 projecting from its outer surface. As shown, the protrusions on each segment are circumferentially aligned and are located next to the end having the recess 27. The protrusions 28 engage the undersurfaces of the models 12 to at least partially support their weight when the set-up 10 is assembled.

In the illustrated embodiment of the invention, the segments 25 are provided with indexing structure which cooperates, when adjacent segments are fitted together, to locate them in a predetermined angular position relative to each other. This indexing structure is shown to comprise a notch or keyway 30 in each of the neck portions 26 and a key 31 extending inwardly from the axial wall of the recess 27. In the illustrated construction wherein each segment 25 has four equally spaced protrusions 28 about its circumference, the key 31 is offset 45° from the notch 30 about the longitudinal axis of the segment. It will be understood that with constructions in which the segments carry a different number of protrusions 28, the keys and notches will be suitably positioned to assure the desired circumferential offset of adjacent protrusions along the length of the assembled segments.

The procedure of assembling the set-up 10 will be largely apparent from the foregoing description. In summary, the models 12, including casts 13, the patterns 15 and the gating systems 16, are connected to the individual segments 25 before they are fitted together. This is accomplished by resting the models 12 on the protrusions 28 so that the terminating portions 18 of the gating systems 16 are next to the outer surfaces of the segments. The models 12 are firmly secured to the protrusions 28 and the outer surfaces of the segments in any suitable manner, as by application of a hot melt adhesive. As explained above, the protrusions provide the support necessary to prevent the relatively heavy dental models from becoming detached from the support member 11 when it is handled. The segmental construction of the support member 11 facilitates the described assembly operation.

After the models 12 have been connected to the segments 25, the segments are fitted together by locating the necks 26 in the recesses 27 and engaging the keys 31 in the notches 30. If desired, the segments may be held together by an adhesive or the like. A pouring cup pattern (not shown) is preferably attached to the lower end of the set-up 10 as viewed in FIG. 1 before using it to make an investment mold.

Figure 8:
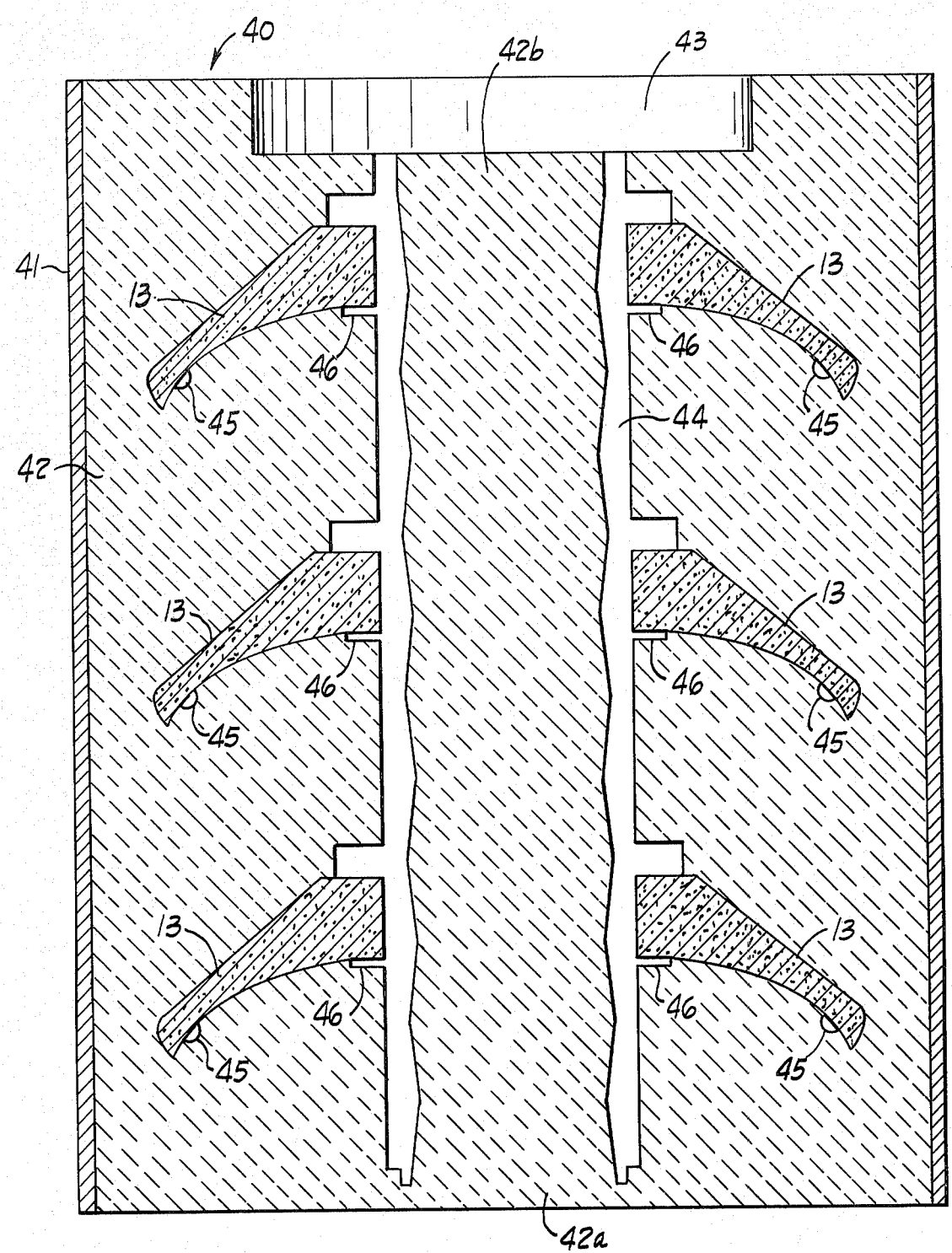
FIG. 8 is a vertical cross-sectional view of a typical refractory mold produced in accordance with the teaching of the present invention.

An investment mold made by use of the set-up 10 is illustrated in FIG. 8 and designated by reference numeral 40. The mold 40 is produced by placing the set-up 10 in a flask 41 so that the set-up is in the upright position shown in FIG. 1 with the pouring cup pattern (not shown) down. The set-up is then invested by filling the flask with refractory slurry which is packed around each of the models 12 and allowed to harden to form a refractory mold body 42. In the production of the illustrated mold 40, the slurry is allowed to fill the inside and cover the top of the support member 11 so that the mold 40 has a closed end 42a and a center core-like portion 42b.

After the slurry has hardened, the support member 10, the patterns 15, the gating systems 16 and the pouring cup pattern are removed or eliminated from the mold 40, as by heating and melting. The elimination of the pouring cup pattern produces a pouring cup 43 which communicates with a generally tubular sprue 44 formed by elimination of the support member 11. The elimination of the patterns 15 and the gating systems 16 produces pattern cavities 45 connected by gates 46 to the sprue 44. It will be understood by those skilled in the art that different variations of molds can be made using the set-up 10. For example, the open end of the support member 11 can be closed before investing it to prevent the formation of the core-like portion 42b. In some instances, a separate core can then be placed into the mold to form the tubular sprue. Alternatively, the center passage of the mold can be filled solid with metal during casting.

It will be seen that the support member 11 is uniquely characterized by its segmental construction which lends itself to an economical injection molding operation using inexpensive tooling and by the presence of the protrusions 28 which make it possible to support a multiple number of the relatively heavy models 12. It will also be seen that circumferential offsetting of the protrusions along the length of the support member facilities assembly of the set-up and the production of a sound investment mold.

Many modifications and variations of the invention will be apparent to those skilled in the art in light of the foregoing detailed disclosure. Therefore, it is to be understood that, within the scope of appended claims, the invention can be practiced otherwise than as specifically shown and described.

What is claimed is:

1. A method of making a plurality of dental castings in a single mold by the lost pattern process of investment casting comprising the steps of:
   a. fitting together in end-to-end relation a plurality of annular segments so as to form a cylindrical support member having outwardly extending, spaced protrusions,
   b. forming patterns of dental castings on refractory casts of anatomical form,
   c. placing said casts on said protrusions,
   d. connecting said patterns to said support member to provide gating structure,
   e. forming a mold around said casts, patterns, gating structure and support member,
   f. thereafter removing said patterns, gating structure and support member from the mold, and
   g. filling the mold with metal to form dental castings on said refractory casts.

2. In the manufacture of dental castings, a method comprising the steps of:
   a. forming a support member having a plurality of outwardly extending, spaced protrusions,
   b. mounting a plurality of refractory dental models on said support member so that said models are engaged on top of and supported by said protrusions,
   c. said models carrying patterns of the dental castings,
   d. attaching the patterns to the support member to provide gating structure,
   e. forming a refractory mold around the models, patterns and gating structure, and
   f. thereafter removing said patterns, gating structure and support member from said mold so that the mold can be filled with metal.

3. A method as claimed in claim 2 wherein said models are mounted on said support member so that adjacent models along the length of said support member are circumferentially offset relative to one another.

4. A method as claimed in claim 2 wherein said support member is formed to include a plurality of individual segments connected together in end-to-end relation.

5. In the manufacture of dental castings, a method comprising the steps of:
   a. forming a support member;
   b. mounting a plurality of refractory dental models on said support member so that adjacent models along the length of said support member are circumferentially offset with respect to one another,
   c. each of said models including a workpiece pattern and a gating system extending to the outer surface of said support member,
   d. covering the assembly of said support member and models with refractory material to form a mold, and
   e. thereafter eliminating said patterns, gating systems and support member from said mold so that it can be filled with metal.

6. A method as claimed in claim 5 wherein said support member is formed to include a plurality of sections connected together in end-to-end relation.

7. A set-up assembly for use in making dental castings by the lost pattern process of investment casting comprising a support member having a plurality of outwardly extending, spaced protrusions, a plurality of refractory casts of anatomical form resting on and supported by said protrusions, patterns of the dental castings carried on said casts, and gating structure connecting said patterns to said support member.

8. A set-up assembly as claimed in claim 7 wherein adjacent casts along the length of said support member are circumferentially offset with respect to one another.

9. A set-up assembly as claimed in claim 7 wherein said support member comprises a plurality of segments assembled in end-to-end relation.

10. A set-up assembly as claimed in claim 9 wherein said segments include cooperating indexing means for rotatively positioning adjacent segments when they are assembled together so that adjacent casts along the length of said support member are circumferentially offset with respect to one another.

11. A set-up assembly as claimed in claim 7 wherein said support member comprises a plurality of sections fitted together in end-to-end relation, said sections including indexing means cooperable when adjacent sections are fitted together to locate them in predetermined angular positions relative to one another.

12. A set-up assembly for use in making dental castings by the lost pattern process of investment casting comprising a support member, a plurality of refractory casts, clustered about and attached to said support member, workpiece patterns carried on said casts, and gate forming means extending across faces of said casts and connecting said patterns to said support member.

13. A set-up assembly as claimed in claim 12 wherein adjacent casts along the length of said support member are circumferentially offset with respect to one another.

14. A set-up assembly as claimed in claim 12 wherein said support member comprises a plurality of sections fitted together in end-to-end relation.

* * * * *

UNITED STATES PATENT AND TRADEMARK OFFICE
CERTIFICATE OF CORRECTION

PATENT NO. : 4,003,423
DATED : January 18, 1977
INVENTOR(S) : Tadaomi J. Shikanai and Robert A. Horton It is certified that error appears in the above-identified patent and that said Letters Patent are hereby corrected as shown below:

On abstract page:

the correct spelling of one of the inventor's name is

--TADAOMI J. SHIKANAI--

Signed and Sealed this

Seventh Day of June 1977

[SEAL]

Attest:

RUTH C. MASON
Attesting Officer

C. MARSHALL DANN
Commissioner of Patents and Trademarks